US00PP28956P2

(12) United States Plant Patent
Cain

(10) Patent No.: US PP28,956 P2
(45) Date of Patent: Feb. 13, 2018

(54) GRAPEVINE NAMED 'IFG TWENTY-FOUR'

(50) Latin Name: ***Vitis* interspecific hybrid**
Varietal Denomination: IFG Twenty-four

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 0 days.

(21) Appl. No.: 15/530,052

(22) Filed: Nov. 28, 2016

(51) Int. Cl.
*A01H 5/08* (2006.01)

(52) U.S. Cl.
USPC ..... Plt./205

(58) Field of Classification Search
USPC ..... Plt./205
See application file for complete search history.

*Primary Examiner* — Annette H Para

(57) ABSTRACT

This invention is a new and distinct grapevine variety denominated 'IFG Twenty-four'. The new grapevine is characterized by producing naturally large seedless light red berries having a narrow ovate shape. Fruits are fairly low in acidity, with very dense firm texture and ripen late in the season.

1 Drawing Sheet

Latin name of the genus and species claimed: *Vitis* interspecific hybrid.

Variety denomination: 'IFG Twenty-four'.

BACKGROUND OF THE INVENTION

The new and distinct grapevine described and claimed herein originated from a hand pollinated cross of the 02108-080-157, an unnamed interspecific seedling selection from the IFG breeding program, and 01032-R Bulk hybridized in May 2007. The abortive seed traces were subsequently embryo cultured and the resulting population of twelve plants was planted in the field in April 2008. The present variety of grapevine was selected as a single plant in September 2009 and was first asexually propagated by hardwood cuttings in December 2009 near Delano, Kern County, Calif. The resulting propagules were planted during April 2010 near Delano, Kern County, Calif. and were found to reproduce true-to-type through at least two generations of asexual reproduction.

BRIEF SUMMARY OF THE INVENTION

The new grapevine 'IFG Twenty-four' is characterized by producing naturally large seedless light red berries having a narrow ovate shape. Fruits normally ripen late season about mid to late September near Delano Calif. Fruits are fairly low in acidity, with very dense firm texture, having no noticeable seed traces. Fruits are moderately susceptible to sunburn damage and may be difficult to color in hot climatic conditions. Attachment of the berry to the pedicel is somewhat weak. Vines are productive and can be pruned to short spurs. Canes produce very little lateral branching allowing sunlight to penetrate the canopy without laborious shoot removal.

The new grapevine differs from its female parent the 02108-080-157 by having larger, lighter red, firmer berries. The exact pollen parent of 'IFG Twenty-four' is unknown because a composite of several similar red skinned selections from the 01032 progeny were bulked together and used to pollinate the 02108-080-157. The 'IFG Twenty-four' can be distinguished from any of the selections in the bulked pollen by having a narrow ovate shape rather than a round or elongated oval shape of the 01032 selections composing the bulked pollen and by having a larger berry size, smaller abortive seed traces and fewer large lateral shoots.

The new grapevine variety 'IFG Twenty-four' is being introduced because of its firm texture, seedlessness, and naturally large berry size.

BRIEF DESCRIPTION OF THE DRAWING

The accompanying photographic drawing illustrates in full color 'IFG Twenty-four'. The photograph was taken outdoors with indirect lighting. The colors are as nearly true as is reasonably possible in a color representation of this type. The right side of the drawing has a shoot tip. A mature fruit cluster is represented in the center of the drawing along with a typical berry in cross section. A mature leaf can be seen on the left side of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2001 by The Royal Horticultural Society, London, England.

Throughout this specification subjective description values conform to those set forth by the International Plant Genetic Resources Institute publication 'Descriptors for Grape' (*vitis* spp.) (1983) which was developed in collaboration with the Office International de la Vigne et du Vin (OIV) and the International Union for the Protection of New Varieties of Plants (UPOV).

The descriptive matter which follows pertains to 'IFG Twenty-four' plants grown in the vicinity of Delano, Kern County, Calif. during 2013 and 2014, and is believed to apply to plants of the variety grown under similar conditions of soil and climate elsewhere:

VINE

General:

*Vigor*.—Vigorous.

*Density of foliage*.—Dense.

*Productivity*.—Productive, producing about 23 to 32 kg of marketable fruit per vine.

*Root stock*.—Own root.

*Training method*.—Typically spur pruned leaving 2 bud spurs.

Trunk:

*Trunk diameter of* 4-*year-old vines at* 30 *cm above the soil line*.—About 4.8 cm.

*Shape*.—Medium to slightly stocky.

*Straps*.—Long-split.

*Surface texture*.—Medium rough texture.

*Inner bark color*.—Greyed-orange: 165A.

SHOOTS

Young shoot:

*Form of tip*.—Wide open.

*Distribution of anthocyanin coloration on tip*.—Piping (striped).

*Intensity of anthocyanin coloration on tip*.—Weak.

*Density of prostrate hairs on tip*.—Very sparse.

*Density of erect hairs on tip*.—Absent.

*Color*.—Yellow-green: 144A.

Woody shoot (mature canes):

*Internode length*.—Medium-long: About 16.8 cm.

*Width at node*.—About 1.2 cm.

*Cross section*.—Circular.

*Surface*.—Slightly striate.

*Main color*.—The following colors were observed: Greyed-orange: 166A and 166B and 166C.

*Density of erect hairs on nodes*.—None.

*Density of erect hairs on internodes*.—None or very sparse.

*Axillary shoot length at full bloom*.—Weak to medium, approximately 11.9 cm.

Flowering shoot:

*Vigor during flowering*.—Medium-strong, producing few lateral shoots.

*Attitude during flowering on shoots not tied*.—Semi-erect.

*Color*.—Dorsal side of internodes — Yellow-green: 146C, with Red-purple stripes: 59B.

*Color*.—Ventral side of internodes — Yellow-green: 146C.

*Color*.—Dorsal side of nodes — Yellow-green: 146C, with Red-purple stripes: 59B.

*Color*.—Ventral side of nodes — Yellow-green: 146C.

*Density of prostrate hairs on nodes*.—None or very sparse.

*Density of erect hairs on nodes*.—None.

*Density of prostrate hairs on internode*.—None.

*Density of erect hairs on internode*.—None.

*Anthocyanin coloration of buds*.—Present.

Tendrils:

*Distribution on the shoot* (*at full flowering*).—Discontinuous.

*Length of tendril*.—Long: about 31.4 cm.

*Thickness of tendril* 2 *cm from base*.—About 1.2 mm.

*Color*.—Yellow-green: N144A.

*Form*.—Trifurcated and quadfurcated.

*Number of consecutive tendrils*.—2.

LEAVES

Young leaves:

*Color of upper surface of first four distal unfolded leaves*.—Yellow-green: 146C with Greyed-red spots: 178B.

*Average intensity of anthocyanin coloration of six distal leaves prior to flowering*.—Weak to medium.

*Density of prostrate hairs between veins* (*lower surface*).—Absent.

*Density of prostrate hairs on veins* (*lower surface*).—Absent to very sparse.

*Density of erect hairs between veins* (*lower surface*).—Absent.

*Density of erect hairs on veins* (*lower surface*).—Absent.

Mature leaves:

*Average length*.—About 14.7 cm.

*Average width*.—About 16.8 cm.

*Mature leaf size*.—Medium.

*Shape of blade*.—Pentagonal.

*Number of lobes*.—5.

*Anthocyanin coloration of main veins on upper side of blade*.—Weak.

*Mature leaf profile*.—Flat to slightly undulate.

*Blistering surface of blade upper surface*.—Very weak.

*Leaf blade tip*.—In the plane of the leaf.

*Undulation of margin*.—Slight.

*Undulation of blade between main and lateral veins*.—Absent.

*Shape of teeth*.—Mixture of both sides straight and both sides convex.

*Length of teeth*.—Short to medium.

*Ratio length/width of teeth*.—Medium.

*Shape of upper lateral sinuses*.—Open to lobes slightly overlapping.

*Depth of upper lateral sinuses*.—Deep.

*General shape of petiole sinus*.—Slightly open to lobes slightly overlapping.

*Shape of base of upper leaf sinuses*.—V-shaped.

*Tooth at petiole sinus*.—Absent.

*Density of prostrate hairs between veins on lower surface of blade*.—Absent to very sparse.

*Density of erect hairs between veins on lower surface of blade*.—Absent.

*Density of prostrate hairs on main veins on lower surface of blade*.—Sparse.

*Density of erect hairs on main veins on lower surface of blade*.—Very sparse.

*Density of prostrate hairs on main veins on upper surface of blade*.—None or very sparse.

*Density of erect hairs on main veins on upper surface of blade*.—None.

*Autumn coloration of leaves*.—Leaves can be a single color or combination of colors, in a mottled pattern or on the edges of the leaves. The following colors were observed: Yellow: 13A and 13B, and Greyed-yellow: 162A, and Purple; N79A and N79B and N79C, and Greyed-purple: 187A and 187B and 187C.

Upper surface:

*Color*.—The following colors were observed: Green: 137A and 137B.

*Anthocyanin coloration of main veins*.—Absent to very weak.

*Surface appearance*.—Dull.

*Blistering surface of blade*.—Very weak.

Lower surface:

*Color*.—The following colors were observed: Yellow-green: 146A and 146B.

*Anthocyanin coloration of main veins* (*lower surface*).—Absent to weak.

*Glossiness*.—Medium.

*Surface texture*.—Smooth.

*Surface appearance*.—Semi-glossy.

Petiole:

*Length*.—About 6.8 cm.

*Length of petiole compared to middle vein*.—Slightly shorter.

*Density of prostrate hairs on petiole*.—None.

*Density of erect hairs on petiole*.—None.

Buds:

*Bud fruitfulness*.—Basal: mostly fruitful.

*Position of first fruitful shoot on previous season cane*.—$1^{st}$ to $2^{nd}$ node.

*Dormant bud length*.—About 5.4 mm.

*Dormant bud width in the proximal/distal plane*.—About 4.6 mm.

*Dormant bud color*.—Greyed-orange: 166A.

*Time of bud burst*.—Midseason: Mar. 7, 2014.

FLOWERS

General:

*Flower sex*.—Hermaphrodite.

*Length of first inflorescence*.—Medium: about 20.8 cm long by 11.6 cm wide.

*Position of first flowering and fruiting node*.—3rd to $5^{th}$ node (current season growth).

*Number of inflorescence per flowering shoot*.—1.1 to 2.

*Time of bloom*.—Midseason as compared with similar varieties in the growing area of Delano, Calif.

*Date of full bloom*.—About Apr. 25, 2014.

FRUIT

General:

*Ripening period*.—Late; Approximately Oct. 3, 2014.

*Use*.—Fresh market.

*Keeping quality*.—Moderate, can be prone to berry shatter during handling and storage at 0° C. and high RH.

*Resistance to*.—Insects: Average typical of *Vitis vinifera* species. Diseases: Average typical of *Vitis vinifera* species.

*Refractometer test*.—Soluble solids: About 16.0 Brix.

*Brix/acid*.—About 36.4.

*Titratable acidity*.—About 0.44.

*Juice ph*.—About 3.6.

Cluster:

*Mature cluster length* (*peduncle excluded*).—About 38.4 cm.

*Mature cluster width*.—About 19.9 cm.

*Mature cluster weight*.—About 1320 g.

*Bunch density*.—Loose.

*Number of berries*.—About 199.

*Form*.—Elongated conical.

Peduncle:

*Lignification of peduncle*.—Weak.

*Length of peduncle*.—Medium long, approximately 4.4 cm.

Berry:

*Uniformity of size*.—Uniform.

*Single berry weight*.—About 8.1 g.

*Shape*.—Narrow ovate.

*Seeds*.—Contains small rudimentary seed traces not noticeable.

*Cross section*.—Circular.

*Berry dimensions*.—Longitudinal axis: about 3.0 cm; horizontal axis: about 2.1 cm.

*Berry firmness*.—Very firm.

*Particular flavor*.—Neutral.

*Bloom* (*cuticular wax*).—Medium.

*Berry separation from pedicel*.—Medium to easy.

*Skin color* (*without bloom*).—Greyed-purple: 187B.

Skin:

*Thickness*.—Medium.

*Skin toughness*.—Somewhat notable when chewing.

*Reticulation*.—Absent.

*Tenacity*.—Tenacious to flesh.

What is claimed:

1. A new and distinct variety of grapevine as herein illustrated and described.

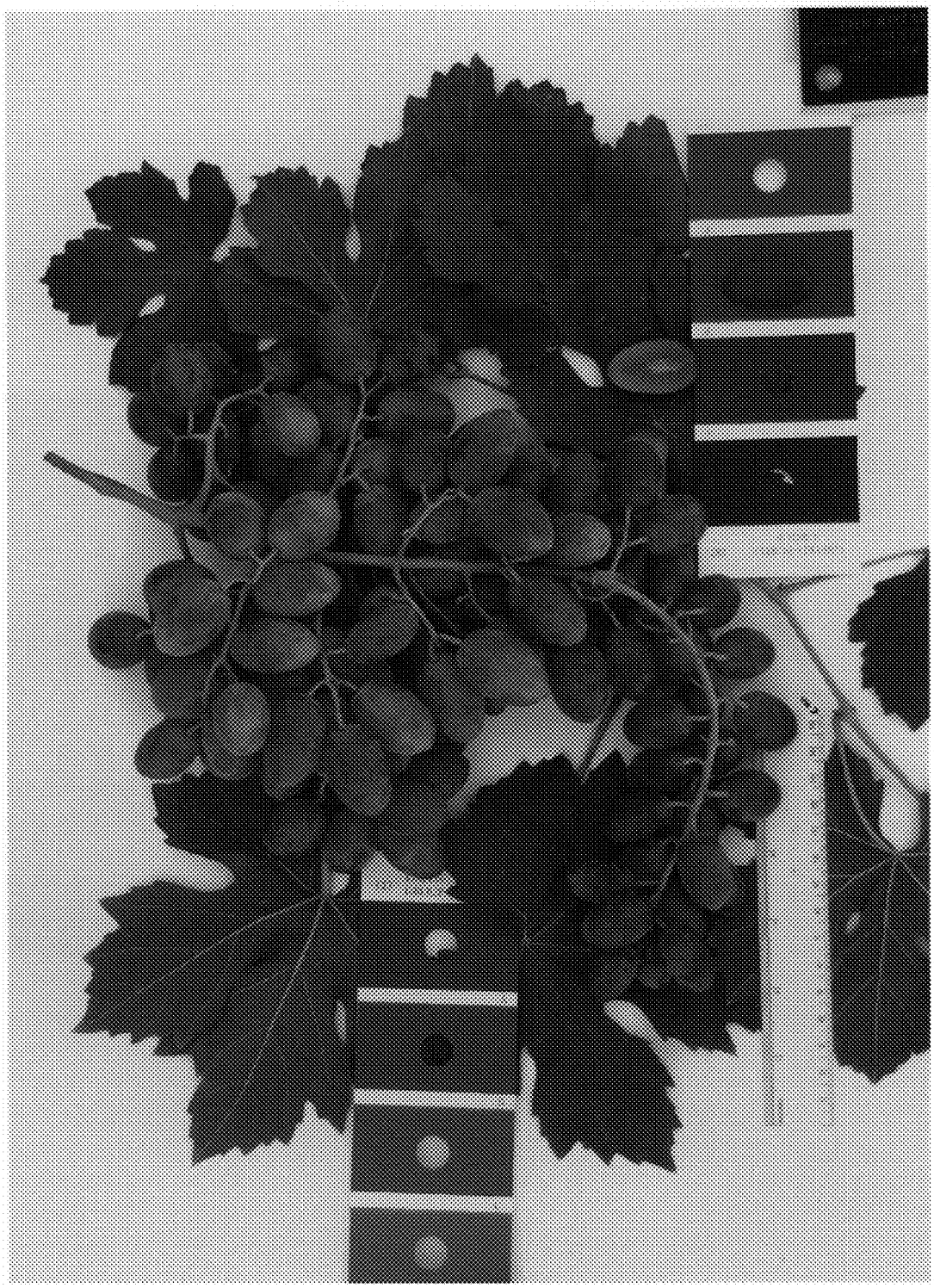

* * * * *